(12) United States Patent
Scholten et al.

(10) Patent No.: US 10,478,164 B2
(45) Date of Patent: Nov. 19, 2019

(54) JAW FOR A SURGICAL TUBULAR SHAFT INSTRUMENT

(71) Applicant: Aesculap AG, Tuttlingen (DE)

(72) Inventors: Thomas Scholten, Tuttlingen (DE); Gunnar Wanke, Kreuzlingen (DE)

(73) Assignee: Aesculap AG (DE)

( * ) Notice: Subject to any disclaimer, the term of this patent is extended or adjusted under 35 U.S.C. 154(b) by 335 days.

(21) Appl. No.: 15/306,277

(22) PCT Filed: Apr. 24, 2015

(86) PCT No.: PCT/EP2015/058948
§ 371 (c)(1),
(2) Date: Oct. 24, 2016

(87) PCT Pub. No.: WO2015/165822
PCT Pub. Date: Nov. 5, 2015

(65) Prior Publication Data
US 2017/0367688 A1    Dec. 28, 2017

(30) Foreign Application Priority Data
Apr. 28, 2014 (DE) .......................... 10 2014 207 900

(51) Int. Cl.
*A61B 17/00* (2006.01)
*A61B 17/128* (2006.01)
(Continued)

(52) U.S. Cl.
CPC .... *A61B 17/00234* (2013.01); *A61B 17/1285* (2013.01); *A61B 17/062* (2013.01);
(Continued)

(58) Field of Classification Search
CPC .......... A61B 17/1285; A61B 17/00234; A61B 2017/2933; A61B 2017/00862;
(Continued)

(56) References Cited

U.S. PATENT DOCUMENTS 5,358,506 A    10/1994  Green
5,858,018 A *   1/1999  Shipp ................. A61B 17/1227
                                                      606/142
(Continued)

FOREIGN PATENT DOCUMENTS

CN      1655726 A      8/2005
CN    102614003 A      8/2012
(Continued)

OTHER PUBLICATIONS

German Search Report for German Application No. 10 2014 207 971.3, dated Mar. 13, 2015 with translation, 15 pages.
(Continued)

*Primary Examiner* — Phong Son H Dang
(74) *Attorney, Agent, or Firm* — RatnerPrestia

(57) ABSTRACT

A jaw assembly for a surgical tubular shaft instrument includes a supporting component, a first arm and a second arm, the first arm and/or the second arm each having one link element. The arms are held by the supporting component in the axial direction. A cam carrier element is axially movable relative to the supporting component and carries at least two cams. Each link element is designed to be in contact with at least two cams when there is a relative axial movement between the supporting component and the cam carrier element, the cams being provided on the cam carrier element. Each link element is further designed to slide off of the cams to effect an opening or closing of the jaw assembly.

15 Claims, 7 Drawing Sheets

(51) Int. Cl.
  *A61B 17/29* (2006.01)
  *A61B 17/062* (2006.01)
  *A61B 17/3201* (2006.01)
  *A61B 17/28* (2006.01)
(52) U.S. Cl.
  CPC ........... *A61B 17/29* (2013.01); *A61B 17/3201* (2013.01); *A61B 2017/00862* (2013.01); *A61B 2017/2808* (2013.01); *A61B 2017/2933* (2013.01); *A61B 2017/2937* (2013.01); *A61B 2017/2939* (2013.01)
(58) Field of Classification Search
  CPC ............ A61B 17/29; A61B 2017/2808; A61B 2017/2937; A61B 2017/2939; A61B 17/062; A61B 17/3201
  See application file for complete search history.

(56) References Cited

U.S. PATENT DOCUMENTS

| | | | |
|---|---|---|---|
| 6,155,988 | A | 12/2000 | Peters |
| 6,228,097 | B1 | 5/2001 | Levinson |
| 6,896,684 | B2 | 5/2005 | Monassevitch et al. |
| 2005/0043757 | A1 | 2/2005 | Arad et al. |
| 2005/0171560 | A1 | 8/2005 | Hughett |
| 2006/0085015 | A1 | 4/2006 | Whitfield et al. |
| 2006/0235437 | A1* | 10/2006 | Vitali .................... A61B 17/10 606/142 |
| 2006/0235442 | A1* | 10/2006 | Huitema ................ A61B 17/10 606/142 |
| 2008/0140090 | A1* | 6/2008 | Aranyi ............... H61B 17/1285 606/143 |
| 2010/0137886 | A1* | 6/2010 | Zergiebel ............. A61B 17/128 606/143 |
| 2011/0087243 | A1* | 4/2011 | Nguyen ............. A61B 17/1285 606/143 |
| 2011/0295270 | A1* | 12/2011 | Giordano ......... A61B 17/00234 606/130 |
| 2012/0197269 | A1 | 8/2012 | Zammataro |
| 2012/0310259 | A1* | 12/2012 | Sorrentino ......... A61B 17/1285 606/143 |
| 2013/0151870 | A1 | 6/2013 | Morales |
| 2014/0379003 | A1* | 12/2014 | Blake, III ............ A61B 17/128 606/143 |
| 2017/0049446 | A1* | 2/2017 | Scholten ............ A61B 17/1285 |
| 2017/0367688 | A1 | 12/2017 | Scholten et al. |

FOREIGN PATENT DOCUMENTS

| | | |
|---|---|---|
| DE | 2744816 | 4/1978 |
| DE | 69220110 | 10/1997 |
| DE | 202010005263 U1 | 6/2010 |
| DE | 102010036713 | 2/2012 |
| DE | 202011109957 U1 | 7/2012 |
| EP | 0945105 | 9/1999 |
| EP | 1712187 | 10/2006 |
| EP | 2481360 | 8/2012 |
| WO | 2006042110 | 4/2006 |
| WO | 2006042141 | 4/2006 |
| WO | 2008118928 | 10/2008 |
| WO | 2008127968 A2 | 10/2008 |

OTHER PUBLICATIONS

Chinese Office Action for Chinese Application No. 201580023303.8, dated Aug. 23, 2018, with translation, 17 pages.
Chinese Office Action for Chinese Application No. 201580021985.9, dated Jul. 31, 2018, with translation, 22 pages.
German Search Report for German Application No. 10 2014 207 900.4, dated Mar. 17, 2015 with translation, 15 pages.
International Search Report and Written Opinion for International Application No. PCT/EP2015/058948, 8 pages.
International Search Report and Written Opinion for International Application No. PCT/EP2015/058942, 10 pages.
Non Final Office Action for U.S. Appl. No. 15/306,291, dated Apr. 11, 2019, 45 pages.
Notice of Allowance for U.S. Appl. No. 15/306,291, dated Oct. 2, 2019, 18 pages.

* cited by examiner

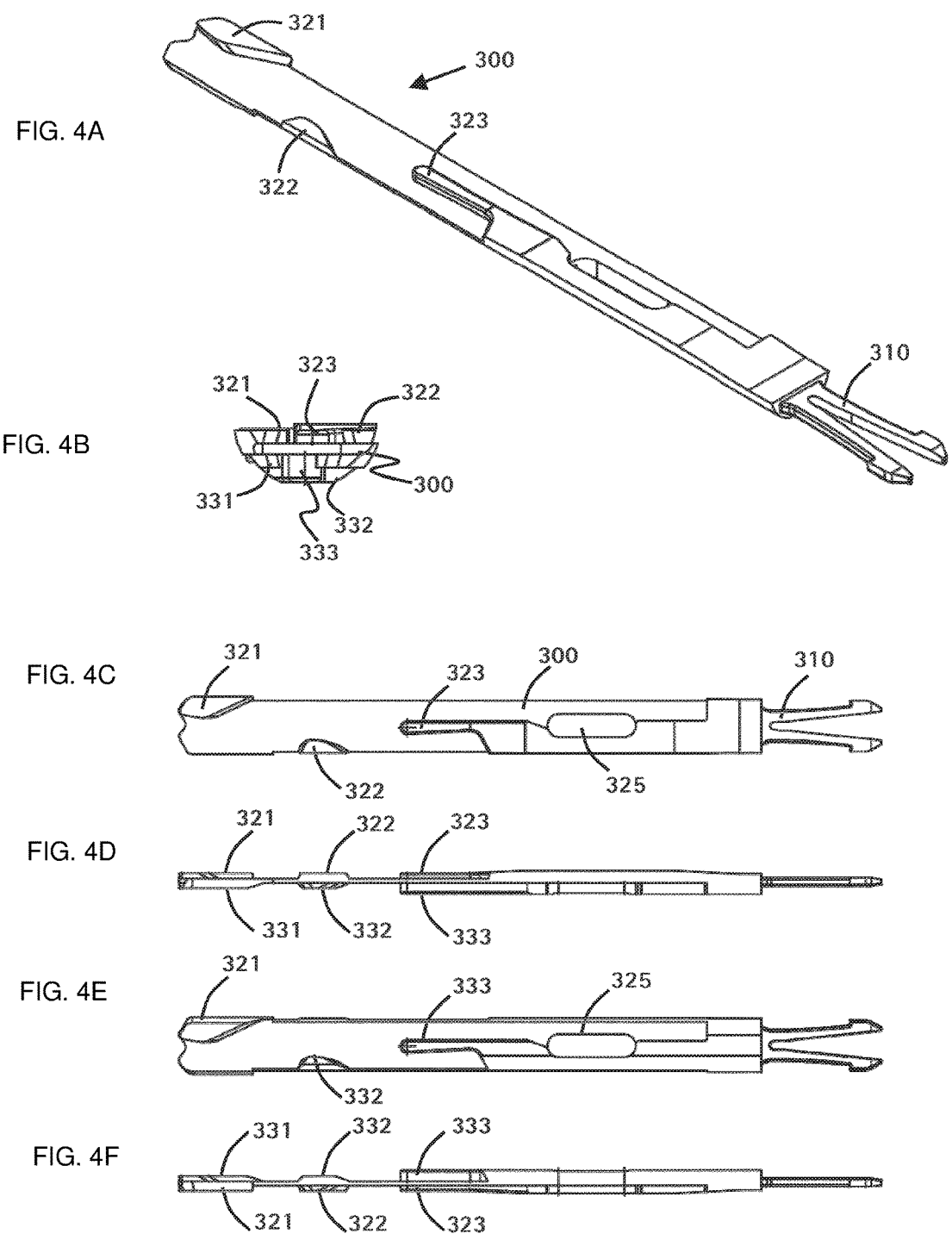

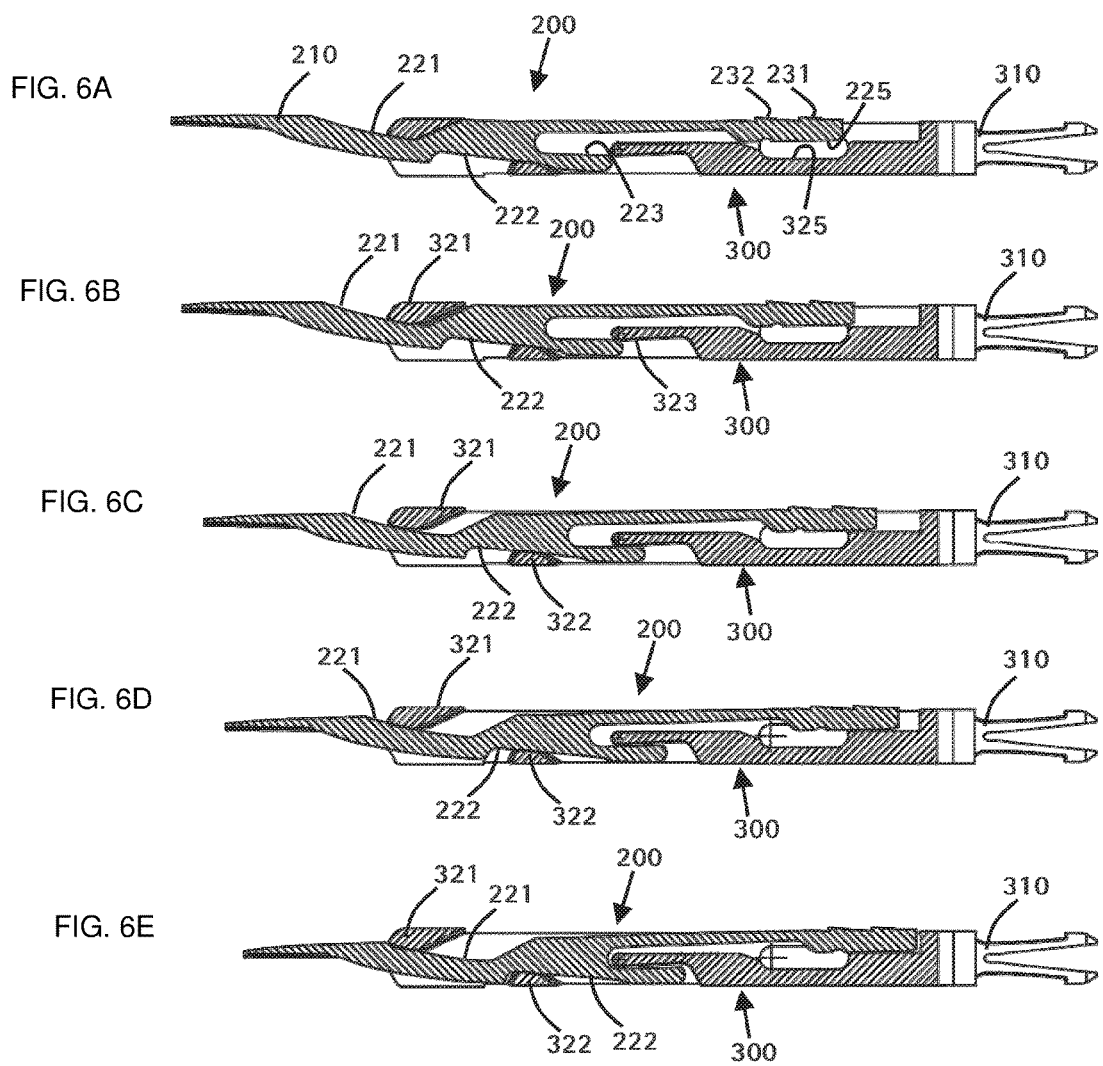

JAW FOR A SURGICAL TUBULAR SHAFT INSTRUMENT

RELATED APPLICATIONS

This application is the U.S. National Phase entry of International Application No. PCT/EP2015/058948, filed Apr. 24, 2015, which claims the benefit of priority of German Application No. DE 10 2014 207 900.4, filed Apr. 28, 2014, wherein the contents of International Application No. PCT/EP2015/058948 and German Application No. DE 10 2014 207 900.4 are incorporated by reference herein in their entireties.

FIELD

The present invention relates to a jaw/mouth assembly for/of a surgical tubular shaft instrument. A surgical tubular shaft instrument is, for example, an endoscopic tubular shaft instrument for applying surgical clips.

BACKGROUND

From the state of the art several jaw assemblies for/of surgical tubular shaft instruments are known. In the European patent application EP 1 712 187 A2, for example, a jaw assembly is illustrated in which the two arms/yaws are resiliently connected by means of a joint basis. In the area of their distal ends that are provided for holding and compressing the surgical clip and in this way applying the clip, each of the two arms includes a sliding surface on its outside. In order to close the jaw assembly and thus to apply the clip the jaw assembly is shifted relative to the shaft in which it is arranged in the proximal direction (the jaw assembly is thus partly pulled into the shaft and, resp., the shaft is slid over the jaw assembly) and the distal edge of the shaft slides off the sliding surfaces. The inclination of the sliding surfaces relative to the axis of the shaft causes the distal ends of the arms to be urged inwardly, while the proximal ends of the arms are held by the basis. In this way, each of the arms performs a rotation about the point at which the arms are connected to the basis. An opening operation of the jaw assembly takes moreover place unguided and is ensured exclusively by the elasticity of the arms urging back into their home position when the jaw assembly is slid out of the shaft during the opening operation.

A comparable jaw is also illustrated in the international patent application WO 2008/127 968, even if the instrument illustrated there is in total strongly different from the afore-described instrument.

The rotation of the arms during opening and closing the jaw assembly is resulting even more clearly from the US patent application US 2005/0171560 A1. There the distal areas of both arms are articulated at the basis and rotate about the mounting point. In this design, too, the clip is applied by the distal edge of the shaft sliding off the sliding surfaces provided on the outsides of the arms and in this way urging the arms inwardly.

The problem of this type of jaw assemblies resides in the fact that they have always the same closing geometry, more exactly speaking that in each case first the distal ends of the arms contact each other and pass by each other and thereafter follows the contact or the bypassing of the further proximally located areas of the arms. In the case of clip appliers this means that the clip is closed in each case from the distal end. For this reason, this structure of a jaw assembly is not useful to other surgical instruments such as, for example, endoscopic scissors.

It is another problem of jaw assemblies of this type that the opening of the jaw assembly is realized solely by the elasticity of the arms. The opening movement of the jaw is carried out unguided. Should a piece of tissue or any other part get between the front edge of the shaft and an arm of the jaw, this might obstruct the opening operation of the jaw assembly. Then the instrument would first have to be removed from the cavity inside the patient so as to be freed from the tissue piece and would subsequently have to be introduced into the patient again. This entails delays and troubles in the operating cycle.

SUMMARY

It is the object of the present invention to provide a jaw assembly for a surgical tubular shaft instrument in which, on the one hand, the closing geometry of the jaw assembly can be freely adjusted and in which, on the other hand, guided closing and opening of the jaw assembly is performed.

The object of the present invention is achieved by a jaw assembly for a surgical tubular shaft instrument according to the present application.

Definition of Terms

The term of the surgical tubular shaft instrument in this application comprises, on the one hand, endoscopic instruments such as endoscopic clip appliers or needle holders. On the other hand, this term also comprises surgical instruments for an open operation in which the functional portion or the active portion of the instrument is separated from the operating portion or the grip portion by a shaft or a shaft-type component. The term shaft or shaft-type component in this context denotes a component whose dimensions and position relative to the actuating portion (e.g. handle piece) are substantially invariable even during actuation of the surgical instrument. An axial displacement along the axis of the shaft or shaft-type component and, resp., a rotation about said axis is admissible, but not a substantial displacement transversely to said axis or rotation relative to said axis in such a way that the two ends of the component substantially move away from this axis. Preferably, the length of a shaft or shaft-type component is larger than the two other dimensions (width, depth) thereof and it has furthermore a preferably slim design. The shaft or the shaft-type component need not be circular, closed, tubular or thin-walled. What is decisive is that it is an instrument which does not have, like a common pair of scissors, a pivot point about which all substantial components of the instrument are rotating, but that the force for opening and closing the jaw assembly is transmitted via an axial movement of a component relative to the shaft.

The functional portion or active portion in this application is the area of the surgical tubular shaft instrument at which the actual function thereof is performed. In the case of a needle holder it is the area which grips and holds the needle, i.e. the distal areas of the arms/yaws/branches. In the case of scissors it is the area which severs the tissue or anything else, i.e. the area at which the two shear edges sliding past each other are formed. In the case of a clip applier it is the area in which the clip is first retained while it is brought to the correct point and into the correct position by the surgeon and in which the clip then is applied, i.e. pressed. In other instruments the definition of the functional portion or active portion is applicable mutatis mutandis.

The active area is the area of one single arm at which the latter brings about the specific function of the instrument, i.e.

in a needle holder it is a gripping portion, in a pair of scissors it is a shear edge and in a clip applier it is a contact area of the clip.

General Description

According to the present invention, a jaw assembly for a surgical tubular shaft instrument comprises a supporting component, a first arm/yaw/branch (later being defined just as "arm") and a second arm/yaw/branch (later being defined just as arm). A surgical tubular shaft instrument in this case does not only denote an endoscopic surgical instrument but also a surgical instrument for open surgery. In the jaw assembly according to the invention, the first arm and/or the second arm each has one link element and the arms are held in the axial direction by the supporting component. When only one arm has a link element, the other arm usually is fixed relative to the shaft of the surgical instrument so that one arm is stationary and the other arm moves toward said stationary arm and/or past the same and away from the same, when the yaw assembly (later being defined just as "yaw") is closed and opened. Moreover, the jaw includes a cam carrier element which is movable relative to the supporting component in the axial direction and carries at least two cams. Each link element is moreover designed to be in contact with at least two cams provided on the cam carrier element, when there is a relative axial movement between the supporting component and the cam carrier element, and is designed to slide off said cams to effectuate an opening or closing of the jaw.

By means of the jaw according to the invention controlled opening and closing of the jaw is possible. In this way the active areas may also temporarily move apart from each other during a closing operation at the beginning or in the course of the closing operation and thus may cause the jaw to widen, i.e. the distance of the two active areas to increase. The closing operation thus need not be a continuous movement in one direction, it is merely important that during the closing operation the function which is assigned as intended to the respective jaw is executed. In this way a clip applier applies a clip by closing the jaw, a pair of scissors cuts e.g. the tissue and forceps grip the object to be gripped equally during the closing operation. Opening corresponds to the opposite operation and consequently e.g. to releasing the tissue by the forceps or, resp., the active areas of the arms of the forceps.

By the jaw according to the invention the opening and closing kinematics of the jaw can be adjusted and in this way adapted to the respective function of the jaw. For example, in the case of a clip applier the jaw can initially be opened a little bit during a closing operation, i.e. the active areas of the arms at first move apart from each other. When using a clip having a certain elasticity which is introduced to the jaw while being somewhat biased when the jaw is in the home position, the clip first widens a little and thus follows the opening of the jaw so that it does not fall out of the jaw. After that, the active areas of the arms are e.g. moved toward each other at first relatively quickly and toward the end of the closing operation, when the clip encloses the vessel to be closed already very tightly and an increased pressing force is required to completely close the clip, the active areas of the arms are moved toward each other more slowly than before so as to ensure sufficient pressing of the clip and thus proper closure of the vessel. In the case of conventional jaws widening is not possible during the closing operation as the conventional jaws are closed by pressing onto the two elastically connected arms laterally from outside. Widening of the jaw cannot be achieved by such design. However, also a controlled opening operation offers advantages which cannot be achieved by the conventional jaws. When the jaw of a conventional instrument is closed and a tissue piece has got jammed between the arms, then the jaw may happen not to open when the surgeon releases the actuating portion of the surgical instrument. This is due to the fact that the opening movement of the jaw is obtained by the elasticity of the arms only. Such elasticity usually is relatively low, because high elasticity would be obstructive during the closing operation. In particular in endoscopic instruments the spatial situation within the instrument is extremely narrow and all components are designed to be as slim as possible. For this reason, an increased spring rigidity of the fastening portions of the arms of the jaws would result in an increased cross-section thereof. At the same time, the component exerting the closing force onto the arms would have to be increased in cross-section. This would result either in an increased overall cross-section of the jaw or in a reduced load capacity of the same when the cross-sections are not adapted. When such jaw does not open any more, the instrument has to be removed from the operating area, e.g. has to be opened manually at the jaw and subsequently inserted at/in the operating area again by the surgeon. This does not only result in a delay in the operating cycle but also represents a potential risk to the patient, on the one hand by the fact that a bleeding possibly cannot be stemmed fast enough and, on the other hand, by a possible introduction of contaminations and pathogens by manipulating the jaw of the instrument and by the subsequent re-insertion into the patient. However, there is also a risk of injury to the person releasing the jaw again, especially when the instrument is a pair of scissors or any other instrument having sharp edges.

This problem will not arise with a jaw according to the invention having controlled opening and closing kinematics. If e.g. a piece of tissue happens to get jammed between the two arms of the jaw or between one arm and the shaft component, sufficient force can be applied by driving the one arm or both arms via the cams and link elements so as to open the jaw without having to remove it from the field of operation. In this way the operating cycle is not delayed and the afore-described risks for patients and the operating surgeon are dropped.

According to an advantageous embodiment of the present invention, the supporting component is formed integrally with a shaft component of the shaft or it is mounted thereto. The cam carrier element moreover is a slide which is axially movable relative to the instrument shaft. This corresponds to an especially advantageous design, as the slide can be arranged inside the shaft or the shaft component. The jaws thus need not axially move relative to the shaft or the shaft component, which facilitates an exact positioning and operation of the jaw to the surgeon.

In accordance with another advantageous embodiment of the present invention, the first arm and the second arm are elastically coupled. In the case of an elastic coupling of the two arms, preferably at the proximal area thereof, especially the assembly of the jaw can be facilitated, as fewer individual components are provided.

In accordance with an especially advantageous embodiment of the present invention, at least two link paths are configured on at least one link element. This configuration enables most various opening and closing kinematics of the jaw to be materialized. In addition, when the cams are sliding along different link paths, the distance thereof from each other may be slightly increased so that a higher moment may be applied to the active area of the respective arm.

In accordance with an advantageous embodiment of the present invention, the first arm and/or the second arm include(s) at least one projection engaging in an area of the supporting component and in this way restricting and preferably preventing an axial movement of the arm relative to the supporting component. This configuration enables an especially simple axial connection of the respective arm to the supporting component. When the supporting component integrally receives the projection in the axial direction of the jaw, the respective arm is axially fixed relative to the supporting component. When the projection is received e.g. in sort of a slotted hole, the axial movement of the arm relative to the supporting component is limited but not completely fixed. It is important in this context that the distance which the arm may cover vis-à-vis the supporting component is smaller than the distance which the cam carrier element moves relative to the supporting component, because otherwise there may be no movement between the cam carrier element and the supporting component and thus no opening and closing operation can be generated. Preferably the respective arm does not move substantially relative to the supporting component in the axial direction.

According to another advantageous embodiment of the present invention, the at least one projection is provided at an resiliency flexible extension of the pertaining link element of the arm and the resiliency flexible extension urges the projection toward the supporting component and in this way secures engagement of the at least one projection in the supporting component, wherein the resilient elasticity of the extension preferably is adjusted so that the mobility and the movements of the link element are not substantially influenced by the extension. Of advantage, the at least one projection of the respective arm is arranged on an elastic extension extending from the arm in the proximal direction, i.e. away from the active area of the arm. Due to its bending elasticity, said extension urges preferably laterally against the supporting component and forces the projection into a seat within the supporting component. The bending elasticity thus secures the projection against slipping or popping out of the seat. Further preferred, the respective arm has two projections which are arranged one behind the other in the axial direction of the jaw. In this way the retaining force which has to be transmitted or absorbed by each projection and the corresponding counter-face of the seat on the supporting component is spread out. Further preferred, the distances between the force transmission surfaces of the two projections are somewhat smaller than the distance of the corresponding counter-faces on the supporting component. When in such design the cam carrier element is shifted in the distal direction so as to cause a closing operation of the jaw, the respective arm is also shifted in the distal direction within the scope of its play. When at first the more proximal projection transmits a retaining force, this causes a moment in the elastic extension which urges the more distal projection against the supporting component. Shortly thereafter also the more distal projection transmits part of the retaining force so that the arm cannot move substantially in the axial direction. However, this arrangement helps to secure the more distal projection twice against slipping or popping out of the seat within the supporting component.

According to another advantageous embodiment of the present invention, at least one link element is configured to be substantially flat, the cam carrier element is also configured to be substantially flat and the at least one link element is substantially adjacent to a flat side of the cam carrier element so that a sandwich structure is formed. Preferably one link element is arranged on both sides of the cam carrier element, i.e. the cam carrier element is arranged between the two link elements. In this manner, a jaw having a very flat structure outside of the area in which the active surfaces are arranged may be designed. This enables access to the active area from the proximal direction so that, in the case of a clip applier, from there e.g. clips may be supplied into the jaw.

In accordance with another advantageous embodiment of the present invention, the cam carrier element and at least one link element form an area in which a link path and the pertaining cam of the cam carrier element form an undercut so that the link element is prevented from lifting off the cam carrier element. When the plane in which the jaw is active is not identical to the plane in which the cam of the cam carrier element is adjacent to the link of the respective arm, a moment causing the link element to lift off the cam carrier element will occur. The undercut between the cam and the link path prevents such lifting, however, so that the sandwich structure of the cam carrier element and the link element will be maintained. Preferably at least one area of an undercut is provided over the entire range of movement of the link element relative to the cam carrier from a completely opened position into a completely closed position of the jaw. Further preferred, an assembling position located outside the range from the completely opened position to the completely closed position of the jaw is provided in which such undercut can be eliminated. The assembling position preferably cannot be adopted by the jaw any more after the latter has been mounted to a shaft or shaft component of a surgical instrument. If no undercut is provided between the cam carrier element and the link element, a component securing the respective components against mutual lift-off, such as a clip, may be provided.

According to an especially advantageous embodiment of the present invention, the surgical instrument is a surgical clip applier and the arms of the jaw are designed to support a surgical clip and to apply the same by closing the jaw. Preferably, the clip is supported and applied by the active areas of the arms. Further preferred, the surgical clip is a double-webbed clip consisting especially of two clip halves being connected to each other only at the two distal ends thereof. The controllable opening and closing kinematics as described before is especially suited for surgical clip appliers, as it is possible by such opening and closing kinematics to apply clips whose maximum lateral dimension at their distal end is larger than the diameter of the jaw in the home position and also larger than the diameter of the shaft of the instrument by an applier.

In accordance with still another advantageous embodiment of the present invention, the arms of the jaw are designed to be shifted in the completely opened position of the jaw by a clip arranged within the jaw outwardly beyond the lateral position of the arms which is adopted by the branches in the completely opened position of the jaw when no clip is arranged in the jaw. By this arrangement the arms are elastically formed between the link element and the active area and/or certain play is provided between at least one cam and the link element. In the latter case the jaw is not only widened by the controlled opening characteristics, however, as described in the foregoing, but the elasticity of the clip is capable of urging the active areas of the arms apart.

In accordance with still another advantageous embodiment of the present invention, on at least one link element at least three link paths are formed, wherein at any given time during the opening and closing operation of the jaw at least two link paths are adjacent to a respective cam provided on the cam carrier. In the case of a clip applier, such design may guarantee a constantly defined position of the respective arms during the closing operation by a contact point of the arm with the clip and two contact points of the arm with two cams being provided, and may guarantee a constantly defined position of the arm during an opening operation by three contact points of the branch with three cams being provided. During the closing movement also three contact points may be present between the arm and three cams and in addition one contact point may be present between the arm and the clip. Speaking of contact points between the arm and the cam refers to the link element of the arm and, resp., to the link paths of the link element.

According to still another advantageous embodiment of the present invention, the jaw comprises a preferably exchangeably mountable clip reservoir in which a plurality of clips is provided, wherein the clip reservoir is disposed at least partly in a plane in parallel to the sandwich structure of the at least one link element and the cam carrier element, with the clips at least partly in the clip reservoir being adapted to be fed to the distal areas of the arms past the sandwich-type layered structure. This structure provides a so called multi-fire jaw adapted to apply a plurality of clips without said clips having to be manually inserted individually into the jaw, for example by having to remove the clip applier from the field of operation, load and then return the same to the field of operation. From the state of the art numerous clip reservoirs and supply principles of automatically introducing a clip into a jaw of a clip applier are known.

According to an advantageous embodiment of the present invention, at least the distal areas of the first arm and of the second arm show a kinematics curve symmetrical to a central axis of the jaw. In this way it can be ensured that the function of the jaw is executed onto its central axis, i.e. in the case of a clip applier the clip is applied exactly centrally between the active areas of the branches and in the case of scissors the cut is carried out exactly along the central axis of the jaw. This improves the handling of the jaw by the surgeon and renders the result of treatment more foreseeable.

According to an advantageous embodiment of the present invention, the surgical instrument is a pair of scissors, a needle holder, a clamp or any other surgical instrument in which two arms are movable toward each other and/or past each other. Accordingly the afore-mentioned instruments having an exactly defined opening and closing characteristic and being definitely superior to the corresponding conventional instruments are provided. As an alternative, the present invention may also be applied to spreader instruments, wherein in the latter the intended function is brought about during the opening operation and not during the closing operation.

According to the invention, consequently a jaw comprising the afore-mentioned features or combinations of individually claimable features is suggested which pertains to the design exhibiting no swivel axes/swivel bolts, i.e. which includes no concrete swivel axis.

BRIEF DESCRIPTION OF THE DRAWING FIGURES

Further advantages and features of the invention are evident to those skilled in the art from the enclosed figures and the detailed description of the embodiments.

FIGS. 4A-4F show a cam carrier element of the jaw according to FIG. 1;

FIGS. 6A-6E show a simplified representation of the first arm and of the cam carrier element according to FIG. 1 in the course of a closing operation;

DETAILED DESCRIPTION

Figure 1A:
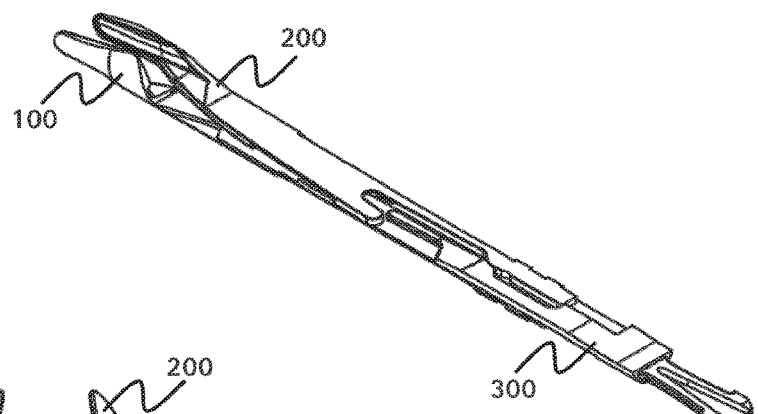
FIGS. 1A-1F show a jaw according to a first embodiment of the present invention.
Figure 1B:
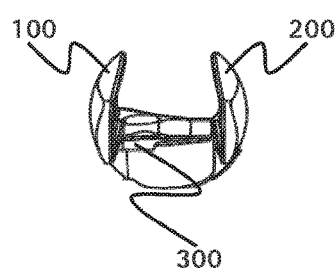
Figure 1C:
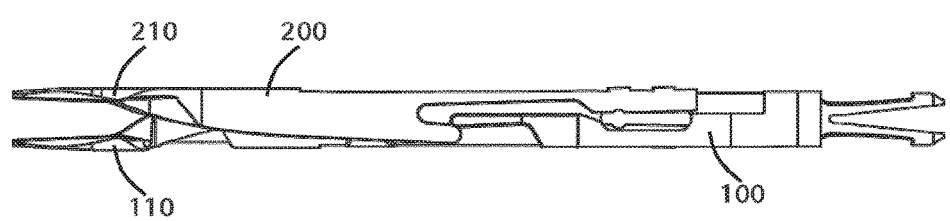
Figure 1D:
Figure 1E:
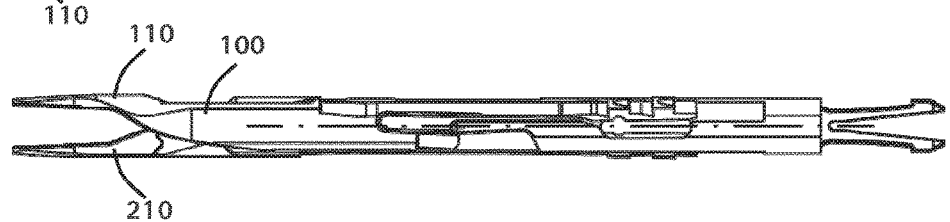
Figure 1F:
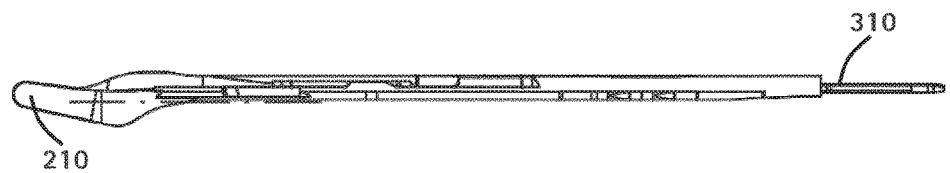
Figure 2A:
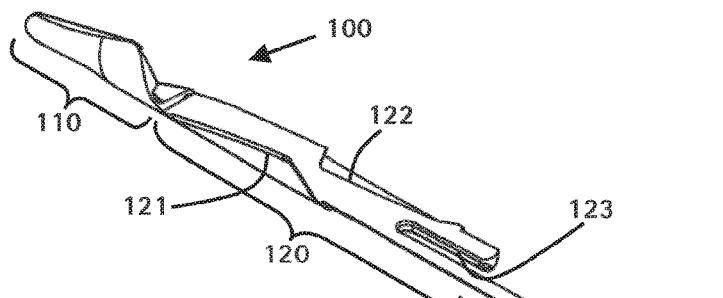
FIGS. 2A-2F show a first arm of the jaw according to FIG. 1.
Figure 2B:
Figure 2C:
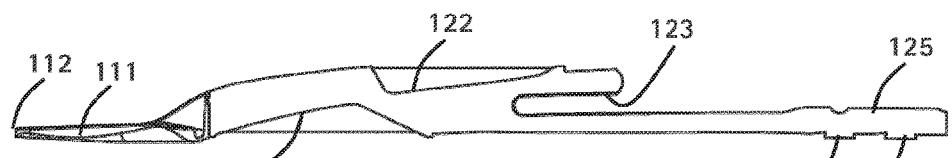
Figure 2D:
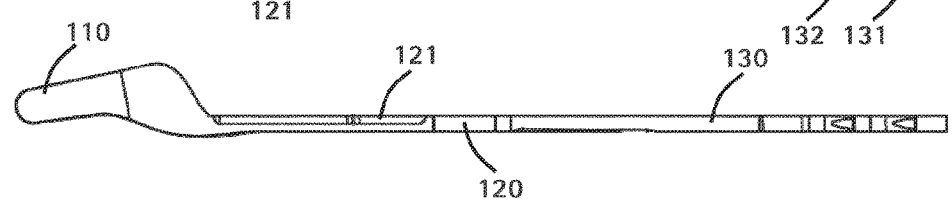
Figure 2E:
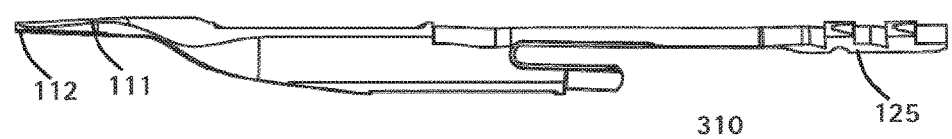
Figure 2F:
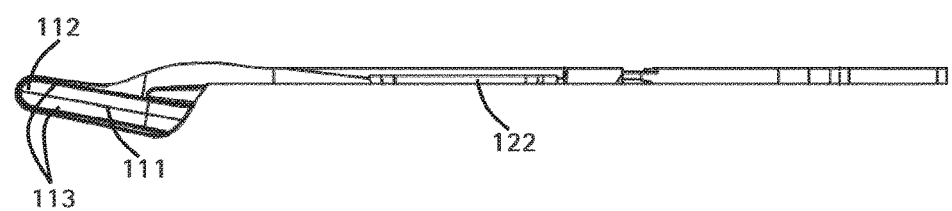
Figure 3A:
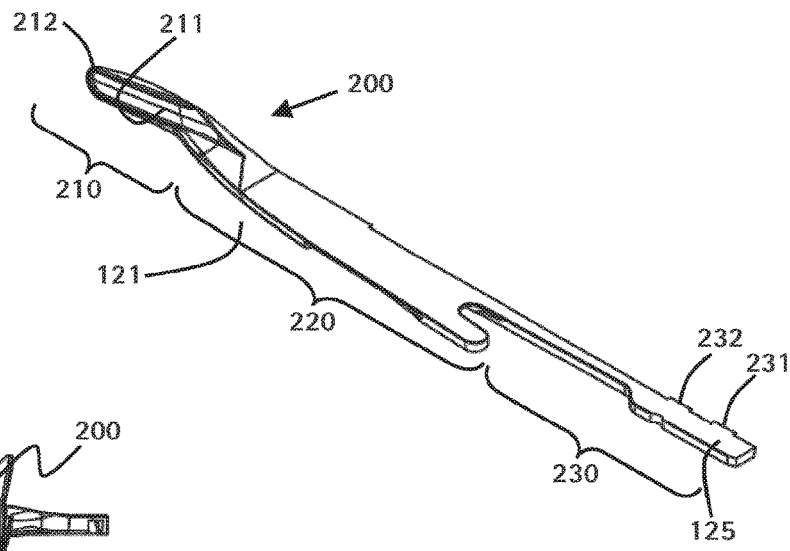
FIGS. 3A-3F show a second arm of the jaw according to FIG. 1.
Figure 3B:
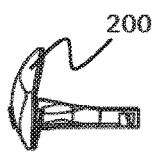
Figure 3C:
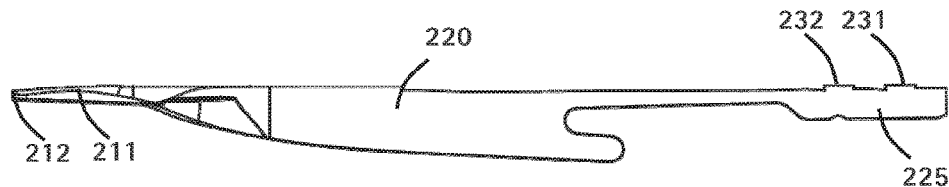
Figure 3D:
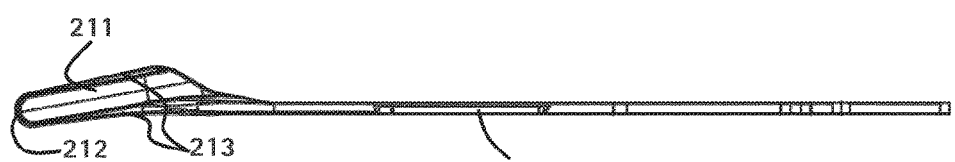
Figure 3E:
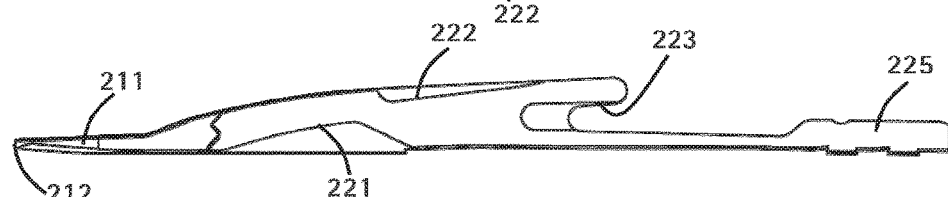
Figure 3F:
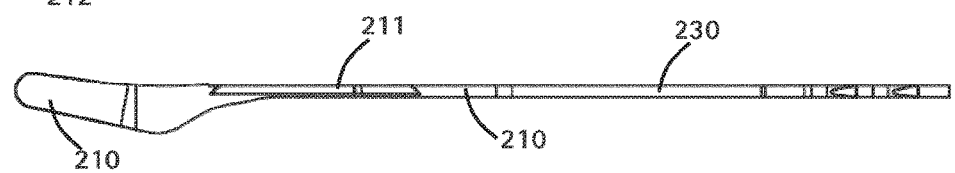

A first embodiment of the present invention is described hereinafter in detail with reference to FIGS. 1A-5F. Each of the FIGS. 1A-5F show in the figure part A an isometric view of the subject matter, in the figure part B a view from the distal end, in the figure part C a top view, in the figure part D a front view, in the figure part E a bottom view and in the figure part F a rear view related to the isometric view.

The first embodiment of the present invention relates to a surgical clip applier and, more exactly speaking, to a surgical clip applicator for double-webbed clips of the multi-fire type (so called multi-fire clip applier). A multi-fire clip applier includes a magazine in which clips are stored and from which after application of the clip provided in the jaw a clip is fed to the latter by means of a feeding mechanism into the jaw and, more exactly, into the active area of the jaw. In contrast to this, a clip applier of the single-fire type (so called single-fire clip applier) includes neither a feeding mechanism nor a magazine. In that case, each clip has to be manually introduced individually into the active area of the jaw of the clip applier. The magazine is mounted to be exchangeable on the shaft of the clip applier. The double-webbed clips used in the embodiment are so called ring clips, i.e. double-webbed clips formed of a ring which is punched out of a metal sheet.

A multi-fire double-webbed clip applier jaw 1 according to this embodiment comprises a supporting component 10. The supporting component 10 in this embodiment is formed by a shaft tube 10 only the lower half of which is shown in FIGS. 5A-5F. The shaft tube 10 is detachably connectable at its proximal end to a handle of the clip applier. The supporting component 10 may also be constituted by another component, however, which is adapted to be arranged on a shaft or shaft component of an applier shaft. In this case the supporting component 10 can be indirectly arranged on a handle of the applier. Slits 12, 13 are provided at the distal end 11 of the shaft tube 10 from which the active areas 110, 210 of arms 100, 200 are projecting. In addition, two recesses 14 and 15 each are provided on both sides in the shaft tube 10.

Each of the first arm 100 as shown in FIGS. 2A-2F and the second arm 200 as shown in FIGS. 3A-3F has an active area 110, 210 as well as a flatly formed link element 120, 220 and a resiliency elastic extension 130, 230, as already illustrated before. The active area 110, 210 of each arm 100, 200 includes a channel 111, 211 in which a surgical clip can be fed from a magazine (not shown) by means of a feeding mechanism (equally not shown) into the active area 110, 210 of the arms 100, 200. A stop 112, 212 is provided to prevent the clip from falling out of the active area 110, 210 of the jaw 1 to the fore (distally). Said stop 112, 212 is adapted to the shape of the distal area of the clip so that the clip is substantially adjacent along its entire distal area to the stop 112, 212 and along a lateral border strip 113, 213 of the channel 111, 211 to the arms 100, 200. The elastic extension 130, 230 extends from the link element 120, 220 of each arm 100, 200 in the proximal direction.

The elastic extension 130, 230 is designed to be resilient especially in its distal area, i.e. where it is connected to the link element 120, 220. In this embodiment an elasticity resulting in a significant lengthening of the extension 130, 230 is not desired. At the proximal end of each elastic extension 130, 230 two projections 131, 132 and, resp., 231, 232 are provided which project from the respective elastic extension 130, 230 in the radial direction. Said projections 131, 132 and, resp., 231, 232 are dimensioned so that they fit into the recesses 14, 15 formed in the shaft tube 10. The elastic extensions 130, 230 are moreover designed so that the proximal ends thereof are urged against the inner wall of the shaft tube by the shape and elasticity of the extensions so that the projections 131, 132 and, resp., 231, 232 are safely accommodated in the recesses 14, 15. For this purpose, the elastic extensions are designed so that the proximal ends thereof extend to be slightly outwardly bent. The elasticity of the extensions is dimensioned so that sufficient urging force is prevailing outwardly in the radial direction to secure the projections 131, 132 and, resp., 231, 232 in the recesses 14, 15, but at the same time the movement of the link elements 120, 220 and of the active areas 110, 210 is not substantially impaired or impeded.

The arms 100, 200 are held to be substantially immobile vis-à-vis the shaft component 10 in the axial direction by the projections 131, 132 and, resp., 231, 232 that engage in the recesses 14, 15 in the shaft component 10.

A cam carrier element 300 as illustrated in FIGS. 4A-4F, which will be referred to as slide in the following, is arranged between the two link elements 120, 220 of the two arms 100, 200. The slide 300 is provided with a fastening strap 310 at its proximal end. Said fastening strap 310 may be inserted in a distal end of a push rod (not shown) and in this way may be permanently fastened to the same. This assembly is especially advantageous for single-use instruments such as the present clip applier. The present clip applier is referred to as single-use instrument despite an exchangeable clip magazine, because it cannot be cleaned and sterilized. For sufficient cleaning the clip applier and hence also the jaw would have to be dismountable, which is not the case with the described connection between the slide 300 and the push rod. Alternatively the push rod may be provided with a fastening strap and the slide may be provided with a corresponding seat or recess. A releasable fastening is possible as well, but it is not provided in this embodiment. With a releasable connection between the slide 300 and the push rod the instrument can also be configured as a reusable instrument.

The push rod can be shifted into the distal direction vis-à-vis the shaft tube by means of an actuating lever or the like provided on a handle (e.g. pneumatic or hydraulic drive). Subsequently, the push rod can be withdrawn into its home position. This reciprocal movement of the push rod relative to the shaft tube 10 causes an opening and closing operation of the jaw.

The cam carrier element or the slide 300 includes on its upper side shown in FIG. 4C three cams 321, 322, 323 and on its lower side shown in FIG. 4E three cams 331, 332, 333. In addition, the slide includes on its upper side a recess 325 and on its lower side a recess 335 which are partly overlapping and thus define a passage in the slide 300.

The upper arm 200 comprises three link paths 221, 222, 223 at its link element 220. At the elastic extension 230 of the upper arm 200 a projection or thickened area 225 is formed substantially opposite to the projections 231, 232. Similarly, three link paths 121, 122, 123 are formed at the link element 120 of the lower arm 100. The elastic extension 130 of the lower arm 100 moreover also includes a projection or thickened area 125 which is configured at the elastic extension 130 to be substantially radially facing away from the projections 131, 132. The two arms 100, 200 and especially the link elements 120, 220 thereof form a sandwich structure with the slide 300.

The cams 321, 322, 323 of the slide 300 are adjacent in the given order to the link paths 221, 222, 223 of the upper arm 200 and during an opening or closing operation slide along the same. It is referred to the fact that not every cam will be in contact with the corresponding link path at any given time of an opening or closing operation. A cam may happen to move away from the link path over a certain range of an opening or closing operation and a gap may happen to be formed between the cam and the pertaining link path. This behavior will be explained in greater detail in the following. It is merely shown here which cam is assigned to which link path. This is also applicable, as a matter of course, to the link paths 121, 122, 123 of the lower arm 100 and the pertaining cams 331, 332, 333 of the slide 300.

Referring to FIGS. 6A-6E, hereinafter an assembly of the jaw 1 as well as an opening and closing operation of the jaw 1 will be described using the example of the upper arm 200. FIGS. 6A-6E illustrate top views of the slide 300 and the upper arm 200, wherein part of the upper arm 200 is cut clear so that the link paths 221, 222, 223 are evident also in the top view. The lower arm 100 behaves corresponding to the upper arm, even though the two arms are not identical, as the lower arm 100 is rounded on its lower side so that it will find its place in the shaft tube 10. The lower arm 100 therefore has been omitted for better understanding of the kinematics of the system in FIGS. 6A-6E. FIG. 6A illustrates the mounting position of the upper arm 200 at the slide 300, i.e. this position of the upper arm 200 and the slide 300 relative to each other cannot be adopted any more once the jaw has been mounted to an instrument shaft and accordingly the slide 300 has been mounted with its fastening strap 310 to a push rod. In the mounting position especially the link path 223 is arranged distally from the cam 323 so that the upper arm 200 in the position shown in FIG. 6A can be rotated anti-clockwise and thus can be removed from the slide 300.

Since in this embodiment the cams 231, 322, 323 of the slide 300 and the link paths 221, 222, 223 of the upper arm form an undercut so that the upper arm cannot lift off the slide 300 even if no retaining clamp is provided, the upper arm 200 cannot be simply attached to the slide 300. Therefore it is important that the upper arm 200 can be rotated in the mounting position relative to the slide 300, as only in this way it is possible to mount the upper arm 200 on the slide 300. The upper arm 200 hence is inclined when being attached to the slide 300 and then is rotated clockwise until the link path 221 gets into contact with the cam 321 and the link path 222 gets into contact with the cam 322. The link paths 221, 222 form undercuts with the cams 321, 322. The lower arm 100 is mounted to the slide 300 based on the same principle. Accordingly, the link paths 121, 122 get into contact with the cams 331, 332 and equally form undercuts.

The two arms 100, 200 and the slide 300 are then inserted from the front side into a shaft tube 10 of an instrument shaft in which a push rod including a recess matching the fastening strap 310 is arranged. In order to allow the arms 100, 200 to be inserted with the slide 300 into the shaft tube 10 the projections 131, 132 and 231, 232 have to be pressed inwardly. To enable this, the two recesses 325, 335 are formed in the slide 300. In the mounting position the thickened portions 125, 225 of the two arms 100, 200 are arranged so that they are located in the axial direction exactly next to the recesses 325, 335. The elastic extensions 130, 230 of the two arms 100, 200 thus may be elastically deformed inwardly so that the thickened portions 125, 225 immerse into the recesses 325, 335. In this way the projections 131, 132 and 231, 232 each provided on the outside are shifted toward the inside so far that the arms 100, 200 can be inserted into the distal end of the shaft tube 10. During insertion the elastic extensions 130, 230 are urging radially outwardly.

When the arms 100, 200 and the slide 300 are progressively inserted into the shaft tube 10, the fastening strap 310 then establishes a connection to a corresponding seat on the push rod in the shaft tube. In this way the slide 300 is permanently connected to the push rod. From this time the slide 300 substantially cannot be pushed any further in the proximal direction into the shaft tube 10. When the arms 100, 200 are continued being pushed into the shaft tube, the arms are displaced also vis-à-vis the slide 300. In this way a contact is made between the cam 323 and the link path 223 of the upper arm 200 and a contact is made between the cam 333 and the link path 123 of the lower arm. In this position the two arms 100, 200 are not rotatable against the slide 300, even if no shaft tube 10 were provided. At the same time, the two thickened portions 125, 225 of the two arms 100, 200 are displaced vis-à-vis the recesses 325, 335 of the slide so that the elastic extensions 130, 230 are urged further outwardly. The two arms 100, 200 may be somewhat further pushed into the shaft tube 10, until the projections 131, 132 are opposed to the recesses 14 and the projections 231, 232 are opposed to the recesses 15. In this position, due to the elasticity of the two extensions 130, 230, the projections 131, 132, 231, 232 immerse substantially simultaneously into the recesses 14, 15 in the shaft tube 10 and thus secure the two arms 100, 200 in the axial direction.

In this embodiment the distance of the two projections 131, 132 is slightly smaller than the distance of the two recesses 14. In this way, when tensile force is applied to the lower arm 100, i.e. when the lower arm 100 is pulled in the distal direction, the tensile force is first transmitted from the projection 131 to the distal wall of the proximal recess 14, thus generating a moment in the extension 130 which additionally urges the projection 132 toward the inner wall of the shaft tube 10. Hence the connection between the lower arm 100 and the shaft tube 10 is further secured. The same principle is also applied to the upper arm 200 so that in this case, too, a tensile force is transmitted first from the projection 231 to the distal wall of the proximal recess 15, before the distal wall of the distal recess 15 engages in the distal wall of the projection 232 and in this way equally transmits forces from the upper arm 200 into the shaft tube 10.

The jaw 1 now is in the home position or zero position shown in FIG. 6B. When the handle of the instrument is actuated, in this embodiment the push rod is pneumatically pushed distally in the shaft tube. Thus also the slide 300 moves in the distal direction. During this movement the cam 321 slides along the link path 221 and shifts the arm 200 and, resp., the active area 210 thereof in FIGS. 6A-6E downwards. The cam 322 slides along the link path 222 and in this way enables the afore-described downward movement of the active area 210. In addition, the cam 323 slides along the link path 223 and stabilizes the position of the arm 200 relative to the slide 300. Since the front part of the arm 200 is laterally displaced while the rear part of the arm is received in the shaft tube 10, it is crucial that the elastic extension 230 of the upper arm has such elasticity that the displacement of the active area 210 is not prevented or significantly impaired by the elastic extension 230. The jaw 1 thus adopts the position shown in FIG. 6C.

With a further progressing closing operation of the jaw 1 the cams 321, 322 continue sliding along the link paths 221, 222, while the cam 323 slightly lifts off or moves away from the link path 223. The shape of the cams 321, 322 and of the link paths 221, 222 is configured so that at the beginning of the closing operation the active area 210 moves inwardly relatively quickly, whereas toward the end of the closing operation the active area 210 moves inwardly more slowly. In this way at the beginning of the closing operation a relatively far distance can be covered relatively quickly, whereas toward the end of the closing operation, when the clip has to be pressed in the jaw 1, a short distance is covered, wherein a great force may be applied to the clip, however. It is not disturbing in this context that at the beginning of the closing operation only a relatively low force can be applied. A position of the upper arm 200 and of the slide 300 during this phase of the closing operation is illustrated in FIG. 6D.

At the end of the closing operation the upper arm 200 and the slide 300 reach the position illustrated in FIG. 6E. In this position the cam 321 and the link path 221 form a maximum contact surface so that in this position also the maximum force can be exerted by the cam 321 on the link path 221 so as to ensure pressing the clip in the active area 210.

During an opening operation the upper arm 200 and the slide 300 pass the positions shown in FIGS. 6A-6E in the reverse order, wherein for example in the position shown in FIG. 6C the cam 323 again contacts the link path 232 and in this way necessarily displaces the active area 210 upwards, i.e. opens the jaw 1 in a forced and guided manner. The opening operation thus is not dependent on an elasticity of an arm or an elastic connection of the two arms in this embodiment. Inter alia, this offers the advantage that the jaw 1 cannot be closed inadvertently e.g. while being introduced to a trocar, for example in that an active area of an arm 100, 200 is pressed against the inner wall of the trocar and then evades radially inwardly to the active area of the other arm. Should this happen, the clip provided in the jaw is pressed and when the jaw 1 widens into the home position again upon leaving the trocar, the clip falls out of the jaw. In the present case, the active area of the arms 100, 200 cannot be inwardly displaced when pressure from outside is applied to the outer sides of the active areas 110, 210, as the cam 323 and, resp., 333 is adjacent to the link path 123 and, resp., 223 and absorbs this force.

The lower arm 100 which is not shown and described here substantially passes the same positions and is subjected to comparable influences by the slide 300. In this embodiment the link paths 121, 122, 123, 221, 222, 223 and the cams 321, 322, 323, 331, 332, 333 are configured so that the two active areas 110, 210 of the two arms 100, 200 move symmetrically to the central axis of the jaw 1.

Moreover this embodiment can be modified so that the jaw 1 initially widens during the closing operation, i.e. initially the two active areas 110, 210 move slightly apart from each other.

Cooperating with an elastic clip which has been introduced in a slightly compressed manner into the jaw 1 and between the active areas 110, 210, in this way an opening of the clip or opening of the jaw can be obtained which cannot be obtained by other instruments having the same shaft diameter. In order to obtain a temporary widening of the jaw 1 in the position shown in FIG. 6C the link path 223 of the upper arm 200 can be displaced upwardly in the contact area with the cam 323 and the link path 221 can be displaced downwardly in the contact area with the cam 321. In such embodiment, the jaw 1 may not widen farther than the clip can follow due to its elasticity, however, as otherwise the clip may fall out of the jaw 1.

Figure 5A:
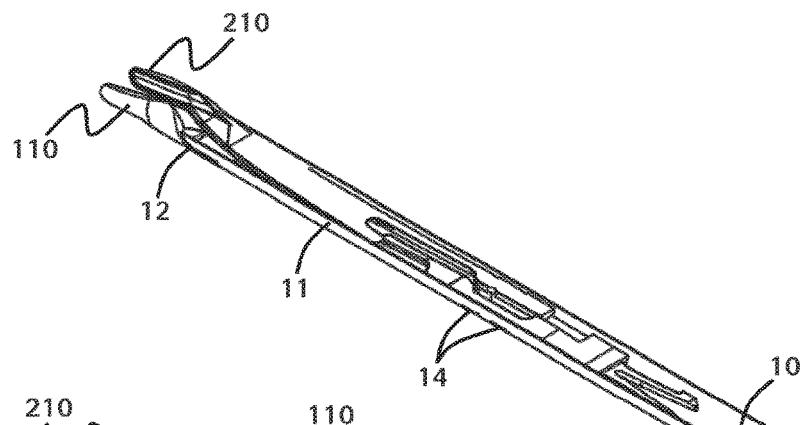
FIGS. 5A-5F show a jaw according to FIG. 1 in a shaft component of an instrument, with the upper half of the shaft component being cut clear.
Figure 5B:
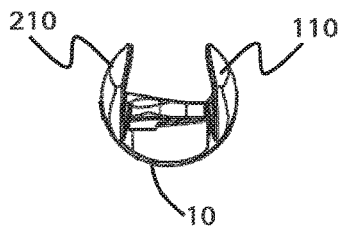
Figure 5C:
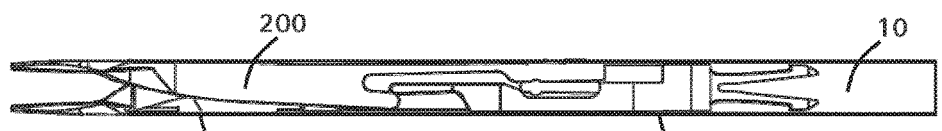
Figure 5D:
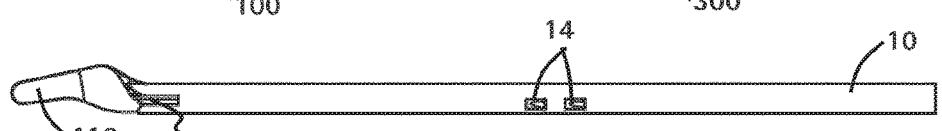
Figure 5E:
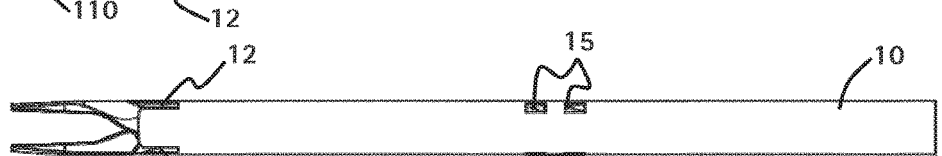
Figure 5F:
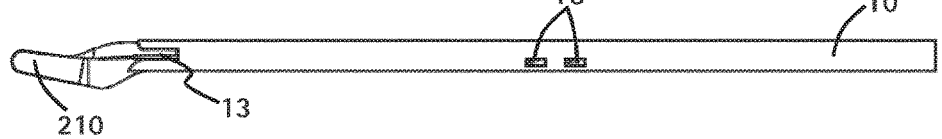

In a view corresponding to FIG. 5A, the clip reservoir and, resp., the clip magazine of this embodiment is arranged above the sandwich-type structure of the two link elements 120, 220 of the two arms 100, 200 and of the slide 300. The individual clips are advanced individually to the active areas 110, 210 of the jaw 1 by means of an advance mechanism not described in detail here, when a clip provided in the jaw 1 before was applied.

Figure 7A:
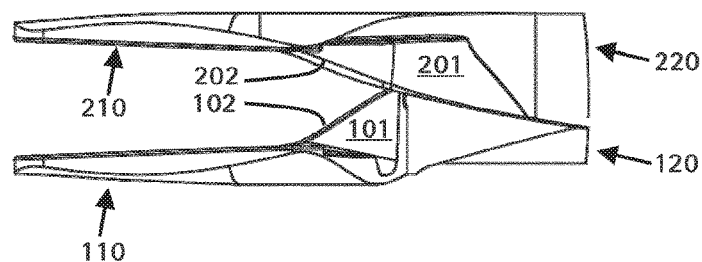
FIGS. 7A and 7B show a detailed top view of the jaw of FIG. 1, with FIG. 7A illustrating an opened state of the jaw and FIG. 7B illustrating a closed state of the jaw.

The jaw 1 of this embodiment includes several special features. A first special feature will be described in detail hereinafter with reference to FIGS. 7A and 7B. In the transitional area 101, 201 between the link element 120, 220 and the active area 110, 210 of each arm 100, 200 each arm is varied from a component planar in the horizontal plane into a component planar substantially in the vertical plane. In order to enable this transitional area 101, 201 to transmit the forces required for pressing a clip, for example, it has to exhibit a particular width in the horizontal lateral direction. Since the arms 100, 200 are sandwiched, however, a shearing effect occurs between the two transitional areas 101, 201, i.e. the distal edges or margins 102, 202 of the transitional area are sliding along each other during a closing operation of the jaw 1. Tissue which happens to get between the two distal edges 102, 202 of the two transitional areas, may thus be inadvertently damaged or even severed. By this effect a vessel to which a clip is intended to be applied may be perforated, which constitutes a high risk to the patient. In order to avert such risk, the transitional areas 101, 201 are configured so that the point at which the two distal edges 201, 202 are superimposed when the jaw 1 is completely closed, is located in the axial direction of the jaw 1 not distally from the proximal end of the clip retained and pressed in the jaw 1.

Figure 7B:
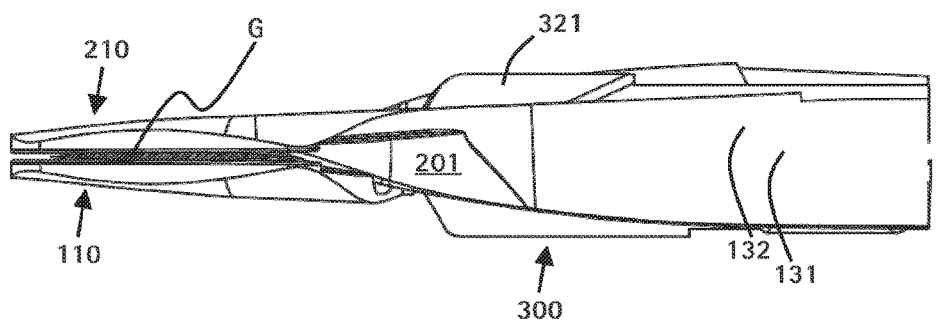

This means that this point is provided in the axial direction level with the clip root or proximally therefrom. When the jaw 1 is opened, the clip root of the clip which is not yet pressed thus is still located ahead of this point. When now tissue G, for example a vessel, is introduced into the jaw 1, it gets preferably into contact with the inner side of the clip root of the clip. In this way the clip prevents the tissue G from being introduced further proximally into the jaw 1. During the closing operation the clip root is somewhat displaced in the proximal direction but never beyond the afore-described point. This ensures that the tissue G will never be damaged by the shearing effect of the two sandwiched link elements 120, 220 and, resp., the transitional area 101, 201 of the arms 100, 200. In FIG. 7B a tissue G is shown which is provided in a closed jaw 1. For the sake of clarity, the clip itself is not shown in FIGS. 7A and 7B. However, it is evident from FIG. 7B that the clip restricts penetration of the tissue G into the jaw 1 and thus protects the tissue G. Under safety aspects, hence this point shall be most proximal in the jaw 1. The farther this point is displaced in the proximal direction, however, the more difficult it is to transmit the required moments to the active areas 110, 210 so as to completely press the clip. Therefore the point is placed in the axial direction exactly level with the clip root in the completely closed state of the jaw. This position of the point entails maximum safety with the lowest possible moments by the active areas 110, 210.

Figure 8A:
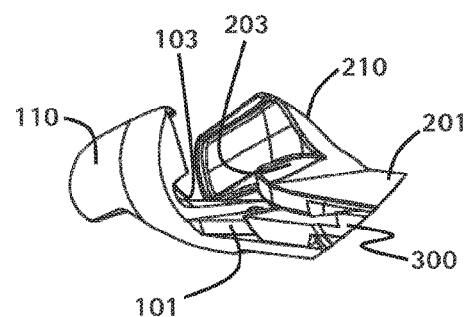
FIGS. 8A and 8B show a perspective view of the jaw of FIG. 1, with FIG. 8A illustrating an opened state of the jaw and FIG. 8B illustrating a closed state of the jaw.
Figure 8B:
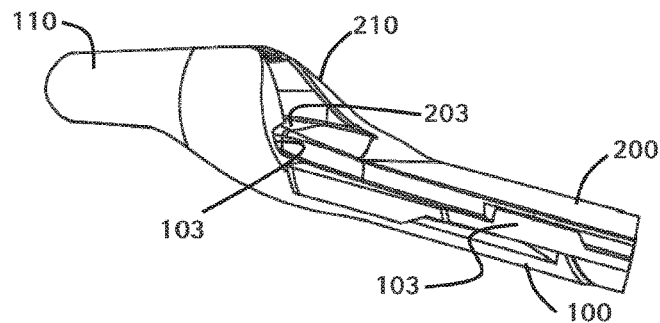

Another special feature of the jaw 1 of the present embodiment is described in detail hereinafter with reference to FIGS. 8A and 8B. This special feature serves for restricting or preventing inadvertent twisting of the two active areas 110, 210 against each other. As is illustrated in FIGS. 8A and 8B, the clip is arranged in the jaw 1 offside a plane in which the force is introduced from the link elements 120, 220 into the active areas 110, 210. Twisting of the active areas 110, 210 against each other, i.e. torsion of each active area outwardly relative to the pertaining link element, results in the fact that an angle is formed between the active areas 110, 210. This would strongly affect the quality of pinching off a vessel by the applied clip. Then the upper webs of a clip in FIGS. 8A and 8B possibly would not be completely pressed against each other and the clip would not sufficiently close the vessel.

Therefore the transitional area 201 of the upper arm 200 has an area 203 facing the transitional area 101 of the lower arm 100. The transitional area 101 of the lower branch 100 includes an indentation 103 which is laterally opposed to the area 203. During the closing operation of the jaw 1 the area 203 immerses into said indentation 103. At the beginning of the closing operation the forces applied by the active areas 110, 210 are relatively small so that no significant twisting of the active areas 110, 210 takes place. At the beginning of the closing operation of the jaw 1 the area 203 is still outside the indentation 103. However, with a progressing closing operation the area 203 enters into the indentation 103 and the shape of the area 203 adapted to the indentation 103 prevents the two active areas 110, 210 from twisting against each other about their respective longitudinal axis. Especially toward the end of the closing operation, when the forces introduced to the active areas 110, 210 are maximal and the arms 100, 200 most strongly tend to twist against each other, the connection of the area 203 and the indentation 103 counteracts this fact.

The invention claimed is:

1. A jaw assembly for a surgical tubular shaft instrument, the jaw assembly comprising:
    a supporting component,
    a first arm including a first active area, and
    a second arm having a second active area,
    each of the first arm and/or the second arm having one link element, the first arm and the second arm being held by the supporting component in an axial direction,
    the jaw assembly further comprising a cam carrier element which is axially movable relative to the supporting component and carries at least two cams,
    said one link element designed to be in contact with the at least two cams when there is a relative axial movement between the supporting component and the cam carrier element, said cams being provided on the cam carrier element, said one link element designed to slide off the at least two cams to effect an opening or closing of the jaw assembly by a movement of the first arm and the second arm directed toward each other or away from each other.

2. The jaw assembly for a surgical tubular shaft instrument according to claim 1, wherein the supporting component is formed integrally with a shaft component of the surgical tubular shaft instrument or is fastened thereto and the cam carrier element is a slide which is axially movable relative to the surgical tubular shaft instrument.

3. The jaw assembly for a surgical tubular shaft instrument according to claim 1, wherein the first arm and the second arm are elastically coupled.

4. The jaw assembly for a tubular shaft instrument according to claim 1, wherein at least two link paths are formed on at least onesaid one link element.

5. The jaw assembly for a surgical tubular shaft instrument according to claim 1, wherein the jaw assembly is of a design exhibiting no swivel axis.

6. A jaw assembly for a surgical tubular shaft instrument, the jaw assembly comprising:
a supporting component,
a first arm including a first active area, and
a second arm having a second active area,
each of the first arm and/or the second arm having one link element, the first arm and the second arm being held by the supporting component in an axial direction,
the jaw assembly further comprising a cam carrier element which is axially movable relative to the supporting component and carries at least two cams,
said one link element designed to be in contact with the at least two cams when there is a relative axial movement between the supporting component and the cam carrier element, said cams being provided on the cam carrier element, said one link element designed to slide off the at least two cams to effect an opening or closing of the jaw assembly by a movement of the first arm and the second arm directed toward each other or away from each other, wherein the first arm and/or the second arm has/have at least one projection which engages in an area of the supporting component and in this way restricts or prevents an axial movement of the first arm and/or the second arm relative to the supporting component.

7. The jaw assembly for a surgical tubular shaft instrument according to claim 6, wherein the at least one projection is provided on a resiliently flexible extension of said one link element and the extension urges the at least one projection toward the supporting component and in this way secures engagement of the at least one projection in the supporting component, with flexibility of the extension being adjusted so that mobility and movements of said one link element and of the first active area and/or the second active area are not influenced by the extension.

8. The jaw assembly for a surgical tubular shaft instrument according to claim 1, wherein said one link element is planar and the cam carrier element is planar, and said one link element is adjacent to a flat side of the cam carrier element so that a sandwich-type structure is formed.

9. A jaw assembly for a surgical tubular shaft instrument, the jaw assembly comprising:
a supporting component,
a first arm including a first active area, and
a second arm having a second active area,
each of the first arm and/or the second arm having one link element, the first arm and the second arm being held by the supporting component in an axial direction,
the jaw assembly further comprising a cam carrier element which is axially movable relative to the supporting component and carries at least two cams,
said one link element designed to be in contact with the at least two cams when there is a relative axial movement between the supporting component and the cam carrier element, said cams being provided on the cam carrier element, said one link element designed to slide off the at least two cams to effect an opening or closing of the jaw assembly by a movement of the first arm and the second arm directed toward each other or away from each other,
wherein said one link element is planar and the cam carrier element is planar, and said one link element is adjacent to a flat side of the cam carrier element so that a sandwich-type structure is formed,
wherein the cam carrier element and said one link element form at least one area in which a link path and the pertaining cam of the cam carrier element form an undercut so that said one link element is prevented from lifting off the cam carrier element, and
wherein at least one area of an undercut is provided over an entire range of movement of said one link element to the cam carrier element from a completely opened position to a completely closed position of the jaw assembly.

10. The jaw assembly for a surgical tubular shaft instrument according to claim 1, wherein the surgical instrument is a surgical clip applier and the first arm and the second arm are adapted to hold and apply a surgical clip by closing the jaw assembly, wherein the surgical clip is a double-webbed clip which includes two clip halves being connected to each other at their two distal ends only.

11. The jaw assembly for a surgical tubular shaft instrument according to claim 10, wherein the first active area and the second active area are designed to be displaced to a completely opened position of the jaw assembly by a clip arranged in the jaw assembly.

12. A jaw assembly for a surgical tubular shaft instrument, the jaw assembly comprising:
a supporting component,
a first arm including a first active area, and
a second arm having a second active area,
each of the first arm and/or the second arm having one link element, the first arm and the second arm being held by the supporting component in an axial direction,
the jaw assembly further comprising a cam carrier element which is axially movable relative to the supporting component and carries at least two cams,
said one link element designed to be in contact with the at least two cams when there is a relative axial movement between the supporting component and the cam carrier element, said cams being provided on the cam carrier element, said one link element designed to slide off the at least two cams to effect an opening or closing of the jaw assembly by a movement of the first arm and the second arm directed toward each other or away from each other,
wherein said one link element is planar and the cam carrier element is planar, and said one link element is adjacent to a flat side of the cam carrier element so that a sandwich-type structure is formed, and
wherein at least three link paths are configured on said one link element of the first arm and/or the second arm, wherein at any given time during an opening and closing operation of the jaw assembly, at least two of the at least three link paths each are adjacent to one.

13. The jaw assembly for a surgical tubular shaft instrument according to claim 12, wherein the jaw assembly includes an exchangeably mountable clip reservoir in which a plurality of clips are provided, the clip reservoir being arranged at least partly in a plane that is in parallel to the sandwich-type structure of the at least one link element and the cam carrier element, wherein the clips can be supplied at least partly in the clip reservoir past the sandwich-type layered structure to the distal arcus of the arms.

14. A jaw assembly for a surgical tubular shaft instrument, the jaw assembly comprising:
- a supporting component,
- a first arm including a first active area, and
- a second arm having a second active area,
- each of the first arm and/or the second arm having one link element, the first arm and the second arm being held by the supporting component in an axial direction,
- the jaw assembly further comprising a cam carrier element which is axially movable relative to the supporting component and carries at least two cams,
- said one link element designed to be in contact with the at least two cams when there is a relative axial movement between the supporting component and the cam carrier element, said cams being provided on the cam carrier element, said one link element designed to slide off the at least two cams to effect an opening or closing of the jaw assembly by a movement of the first arm and the second arm directed toward each other or away from each other,
- wherein the first active area of the first arm and the second active area of the second arm exhibit a kinematics curve symmetrical to a central axis of the jaw assembly.

15. A jaw assembly for a surgical tubular shaft instrument, the jaw assembly comprising:
- a supporting component,
- a first arm including a first active area, and
- a second arm having a second active area,
- each of the first arm and/or the second arm having one link element, the first arm and the second arm being held by the supporting component in an axial direction,
- the jaw assembly further comprising a cam carrier element which is axially movable relative to the supporting component and carries at least two cams,
- said one link element designed to be in contact with the at least two cams when there is a relative axial movement between the supporting component and the cam carrier element, said cams being provided on the cam carrier element, said one link element designed to slide off the at least two cams to effect an opening or closing of the jaw assembly by a movement of the first arm and the second arm directed toward each other or away from each other,
- wherein the surgical tubular shaft instrument is a pair of scissors, a needle holder, a clamp or any other surgical instrument in which two arms are movable toward each other and/or past each other.

* * * * *